(12) United States Patent
Wen et al.

(10) Patent No.: US 11,964,937 B2
(45) Date of Patent: Apr. 23, 2024

(54) (METH)ACROLEIN OXIDATION CATALYST AND PREPARATION METHOD THEREOF

(71) Applicant: Shanghai Huayi New Material Co., Ltd., Shanghai (CN)

(72) Inventors: Xin Wen, Shanghai (CN); Ge Luo, Shanghai (CN); Xinlei Jin, Shanghai (CN); Tonghao Wu, Shanghai (CN); Yan Zhuang, Shanghai (CN); Zhigang Qian, Shanghai (CN); Xiaodong Chu, Shanghai (CN)

(73) Assignee: Shanghai Huayi New Material Co., Ltd., Shanghai (CN)

( * ) Notice: Subject to any disclaimer, the term of this patent is extended or adjusted under 35 U.S.C. 154(b) by 965 days.

(21) Appl. No.: 16/959,647

(22) PCT Filed: Jan. 17, 2019

(86) PCT No.: PCT/CN2019/072085
§ 371 (c)(1),
(2) Date: Jul. 1, 2020

(87) PCT Pub. No.: WO2019/134715
PCT Pub. Date: Jul. 11, 2019

(65) Prior Publication Data
US 2021/0078929 A1    Mar. 18, 2021

(30) Foreign Application Priority Data
Jan. 2, 2018    (CN) .......................... 201810001362.0

(51) Int. Cl.
| C07C 51/25 | (2006.01) |
| B01J 21/06 | (2006.01) |
| B01J 21/18 | (2006.01) |
| B01J 27/199 | (2006.01) |
| B01J 35/00 | (2006.01) |
| B01J 35/06 | (2006.01) |
| B01J 37/00 | (2006.01) |
| B01J 37/04 | (2006.01) |
| B01J 37/08 | (2006.01) |

(52) U.S. Cl.
CPC .......... *C07C 51/252* (2013.01); *B01J 21/063* (2013.01); *B01J 21/18* (2013.01); *B01J 27/199* (2013.01); *B01J 35/0013* (2013.01); *B01J 35/06* (2013.01); *B01J 37/0009* (2013.01); *B01J 37/04* (2013.01); *B01J 37/088* (2013.01)

(58) Field of Classification Search
CPC ........ B01J 21/063; B01J 21/18; B01J 27/199; C07C 21/252
USPC .......................... 502/214, 208–211, 312, 321
See application file for complete search history.

(56) References Cited

U.S. PATENT DOCUMENTS

| 5,215,952 A * | 6/1993 | Bielmeier ............. C07C 51/252 502/209 |
| 2002/0198103 A1* | 12/2002 | Kasuga ................ B01J 23/8885 502/305 |
| 2011/0100876 A1 | 5/2011 | He |
| 2012/0065427 A1 | 3/2012 | Sudo |
| 2014/0316160 A1 | 10/2014 | Iijima |
| 2015/0105583 A1 | 4/2015 | Sakai |

FOREIGN PATENT DOCUMENTS

| CN | 1232814 A | 10/1999 | |
| CN | 1810750 A | 8/2006 | |
| CN | 101579631 A | 11/2009 | |
| CN | 103831131 A | 6/2014 | |
| CN | 104001543 A | 8/2014 | |
| CN | 104646014 A | 5/2015 | |
| CN | 105435805 A | 3/2016 | |
| CN | 105772087 A | 7/2016 | |
| CN | 106881101 A | 6/2017 | |
| CN | 106881128 A | 6/2017 | |
| EP | 0495504 A2 * | 7/2022 | ............. C07C 57/05 |
| JP | H07251075 A * | 10/1995 | ............. B01J 27/186 |
| JP | 2003010690 A * | 1/2003 | ............. B01J 27/199 |
| JP | 2010058288 A * | 3/2010 | ............... B28B 3/20 |
| JP | 2010120241 A * | 6/2010 | ............. B01J 27/199 |

OTHER PUBLICATIONS

Sui, Z. et al., "Study on Oxidative Dehydrogenation of Propane Catalyzed by Phosphorus Oxide Catalyst Supported on Nanocarbon Fiber" (Natural Gas Chemical Industry, vol. 30, No. 5, 2005). English Abstract.
International Searching Authority. Translation of the International Search Report for application PCT/CN2019/072085, dated Apr. 9, 2019.
China National Intellectual Property Association. Translation of Notice on the First Office Action for application 201810001362.0, dated Nov. 5, 2020.

* cited by examiner

Primary Examiner — Patricia L. Hailey
(74) Attorney, Agent, or Firm — Quarles & Brady LLP

(57) ABSTRACT

A (methyl)acrolein oxidation catalyst and a preparation method therefor-in which the catalyst has a composition represented by the following formula: x(Mo12PaCsbVcDeOf)+tC/yZ in which $Mo_{12}P_aCs_bV_cD_eO_f$ is a heteropolyacid salt main catalyst; C is a nano carbon fiber additive, and Z is a carrier thermal conduction diluent; Mo, P, Cs, V, and O represent the elements of molybdenum, phosphorus, cesium, vanadium, and oxygen, respectively; D represents at least one element selected from the group consisting of copper, iron, magnesium, manganese, antimony, zinc, tungsten, silicon, nickel, and palladium; a, b, c, e, and f represent the atomic ratio of each element, a=0.1-3, b=0.01-3, c=0.01-5, e=0.01-2, and f being the atomic ratio of oxygen required to satisfy the valence of each of the described components; x and y represent the weights of the main catalyst and the carrier thermal conduction diluent Z, and y/x=11.1-50%; and t represents the weight of the nano carbon fiber, and t/x=3-10%.

10 Claims, No Drawings

(METH)ACROLEIN OXIDATION CATALYST AND PREPARATION METHOD THEREOF

CROSS-REFERENCE TO RELATED APPLICATIONS

This application represents the U.S. national stage entry of International Application No. PCT/CN2019/072085 filed Jan. 17, 2019, which claims priority to Chinese Application No. 201810001362.0 filed Jan. 2, 2018, the disclosure of which is incorporated herein by reference in its entirety and for all purposes.

TECHNICAL FIELD

The present disclosure relates to a heteropolyacid salt catalyst for preparing (meth)acrylic acid from (meth)acrolein, and a synthesis method thereof. The catalyst has the advantages of high activity, high selectivity and long service life.

BACKGROUND ART

Methyl methacrylate (MMA) is an important organic chemical raw material, mainly used to produce polymethyl methacrylate (PMMA) or organic glass.

In addition, methyl methacrylate is also used in coatings, adhesives, lubricants, wetting agents, printing and dyeing aids, insulating pourable materials, etc. The main process used for production of methyl methacrylate is the acetone cyanohydrin process. However, this process entails the use of hydrocyanic acid, a highly toxic substance, as one of the raw materials, and a large amount of ammonium bisulfate is co-produced, causing a great threat to the environment. After the 1980s, Nippon Shokubai Kagaku Kogyo Co., Ltd. (Japan Catalyst Chemical Company) took the lead to build a unit for production of methyl methacrylate using isobutylene as a raw material (C4 process). Due to the low environmental threat and low production cost, this process has become the second largest production process of methyl methacrylate in the world. In this process, isobutylene is first oxidized to form methacrolein (MAL), then oxidized to form methacrylic acid (MAA), and finally esterified with methanol to form methyl methacrylate (MMA).

Catalysts for oxidizing MAL to MAA are known in the art. For example, US20150105583, US20140316160, US20120065427, etc. disclose the use of heteropoly acid/heteropolyacid salt catalysts to oxidize MAL to MAA. The disadvantages of these catalysts include low yield and short service life.

Chinese Patent Application No. CN104001543A discloses a method for synthesis of a heteropolyacid salt having a core-shell structure, wherein the core is a cesium salt of molybdovanadophosphoric acid or an ammonium salt of molybdovanadophosphoric acid; the secondary outer layer is ammonium molybdovanadophosphate or cesium molybdovanadophosphate; and the outermost layer is a transition metal salt of molybdovanadophosphoric acid. Although this catalyst overcomes some of the shortcomings of conventional heteropolyacid/heteropolyacid salt catalysts, the synthesis process of this catalyst is cumbersome, and the production efficiency is low. Therefore, development of catalysts with better catalytic performance is imperative.

Nanocarbon fiber is a new type of carbon material. Because of its unique structure and properties, it is envisioned to have important application prospects in the fields of materials, catalysis, etc. As a catalyst support material, nanocarbon fiber not only has the properties of activated carbon, carbon black and other traditional carbon materials suitable for catalyst supports, such as large specific surface areas, acid and base resistance, etc., but also has the characteristics of dominating mesoporosity, high electrical conductivity and so on.

Zhijun Sui, et al., "Study on Oxidative Dehydrogenation of Propane Catalyzed by Phosphorus Oxide Catalyst Supported on Nanocarbon Fiber" (Natural Gas Chemical Industry, Vol. 30, No. 5, 2005) discloses the use of a nanocarbon fiber supported phosphorus oxide as a catalyst for catalytic oxidation of propane. Although the use of nanocarbon fiber instead of, for example, activated carbon as a support helps to improve the catalytic performance, the article mentions that "when the loading increases (e.g., from 5 to 15% by weight), the catalytic activity decreases significantly, while the propylene selectivity is merely slightly increased, but it is overall not conducive to increasing the propylene yield. The decrease in activity may be partly attributed to the decreased specific surface area, but it is more likely that the increased loading of the phosphorus oxide on the nanocarbon fiber causes loss of active centers."

Therefore, there is a need in the art to provide a method for modifying a heteropoly acid/heteropolyacid salt catalyst for oxidation of (meth)acrolein to prepare (meth)acrylic acid, so as to further improve the activity, selectivity and stability of the catalyst by means of the modification.

There is also a need in the art to provide a modified heteropolyacid/heteropolyacid salt catalyst for oxidation of (meth)acrolein to prepare (meth)acrylic acid.

SUMMARY

An object of the present disclosure is to provide a method for modifying a heteropolyacid/heteropolyacid salt catalyst for oxidation of (meth)acrolein to prepare (meth)acrylic acid, so as to further improve the activity, selectivity and stability of the catalyst by means of the modification.

Another object of the present disclosure is to provide a modified heteropolyacid/heteropolyacid salt catalyst for oxidation of (meth)acrolein to prepare (meth)acrylic acid.

Therefore, in one aspect of the present disclosure, there is provided a heteropolyacid salt catalyst for preparing (meth)acrylic acid by oxidation of (meth)acrolein, wherein the catalyst has a composition represented by the following formula:

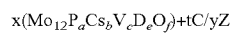

$$x(Mo_{12}P_aCs_bV_cD_eO_f) + tC/yZ$$

wherein $Mo_{12}P_aCs_bV_cD_eO_f$ is a primary catalyst of heteropolyacid salt, C is a nanocarbon fiber additive, and Z is a support/heat-conducting diluent;

Mo, P, Cs, V and O represent elements of molybdenum, phosphorus, cesium, vanadium and oxygen respectively;

D represents at least one element selected from the group consisting of copper (Cu), iron (Fe), magnesium (Mg), manganese (Mn), antimony (Sb), zinc (Zn), tungsten (W), silicon (Si), nickel (Ni), and palladium (Pd);

Z is a support/heat-conducting diluent, which is one of or a mixture of more than one of SiC, $SiO_2$, $MoO_3$, $WO_3$, or $TiO_2$, preferably one of or a mixture of more than one of SiC, $MoO_3$, or $TiO_2$;

a, b, c, e, and f represent the atomic proportions of the elements, wherein a=0.1-3, b=0.01-3, c=0.01-5, e=0.01-2, and f is an atomic proportion of oxygen needed to satisfy the valences of the above components;

x, y represent weights of the primary catalyst and the support/heat-conducting diluent Z, y/x=11.1-50%; and t represents a weight of the nanocarbon fiber, t/x=3-10%.

Another aspect of the present disclosure relates to a method for preparing the heteropolyacid salt catalyst for preparing (meth)acrylic acid by oxidation of (meth)acrolein, wherein the method comprises steps of:

(a) stoichiometrically mixing a molybdenum precursor compound solution, a phosphorus precursor compound solution and a vanadium precursor compound solution to form Solution A; and stoichiometrically mixing a cesium precursor compound solution and a copper precursor compound solution to form Solution B;

(b) mixing Solution A and Solution B, adding a nanocarbon fiber, and drying to obtain a dried body; and (c) mixing the dried body with a support/heat-conducting diluent, followed by shaping and baking.

DETAILED DESCRIPTION

In the present disclosure, the term "(meth)acrolein" refers to methacrolein, acrolein and a mixture thereof.

In the present disclosure, the term "(meth)acrylic" refers to acrylic acid, methacrylic acid, $C_1$-$C_4$ alkyl esters thereof, and mixtures thereof in any ratios.

In the art, the term "composite oxide" refers to a multi-component oxide, wherein at least one component thereof is a transition metal oxide. A composite oxide for a catalytic reaction is a composite oxide catalyst. Composite oxides include heteropolyacids, heteropolyacid salts, homopolyacids, homopolyacid salts, oxyacid salts, spinels, and the like.

A. Catalyst

The present disclosure relates to a heteropolyacid salt catalyst for preparing (meth)acrylic acid by oxidation of (meth)acrolein. The catalyst of the present disclosure has a composition represented by the following formula:

$$x(Mo_{12}P_aCs_bV_cD_eO_f)+tC/yZ$$

In other words, the catalyst of the present disclosure is consisting of three parts: a heteropolyacid salt primary catalyst $Mo_{12}P_aCs_bV_cD_eO_f$, a nanocarbon fiber additive or nanocarbon fiber modifier, and a support/heat-conducting diluent.

1. Heteropolyacid Salt Primary Catalyst $Mo_{12}P_aCs_bV_cD_eO_f$

In the heteropolyacid salt primary catalyst of the present disclosure, Mo, P, Cs, V and O represent molybdenum, phosphorus, cesium, vanadium and oxygen elements; D represents at least one element selected from the group consisting of copper (Cu), magnesium (Mg), manganese (Mn), iron (Fe), antimony (Sb), zinc (Zn), tungsten (W), silicon (Si), nickel (Ni), and palladium (Pd).

a, b, c, e and f represent the atomic proportions of the elements;

a=0.1-3, preferably 0.3-2.5, more preferably 0.5-2.1, desirably 0.8-1.8, most preferably 1-1.5;

b=0.01-3, preferably 0.05-2.5, more preferably 0.1-2.2, desirably 0.2-1.8, most preferably 0.8-1.0;

c=0.01-5, preferably 0.05-4, more preferably 0.1-3.5, desirably 0.5-3.0, most preferably 1-2;

e=0.01-2, preferably 0.05-1.8, more preferably 0.1-1.3, desirably 0.2-1, most preferably 0.5-0.8;

f is an atomic proportion of oxygen needed to satisfy the valences of the above components.

In a preferred embodiment of the present disclosure, the primary catalyst is selected from the group consisting of $Mo_{12}P_{1.5}V_{0.6}Cs_{1.5}Cu_{0.3}$, $Mo_{12}P_{1.5}Zn_{0.3}Pd_{0.05}$, $Mo_{12}P_{1.5}V_{0.6}Cs_{1.5}Cu_{0.3}Sb_{0.2}$, $Mo_{12}P_{1.5}V_{0.6}Cs_{1.5}Zn_{0.3}W_{0.2}$, $Mo_{12}P_{1.5}V_{0.6}Cs_{1.5}Cu_{0.3}Mg_{0.2}$, $Mo_{12}P_{1.5}V_{0.6}Cs_{1.5}Cu_{0.25}Pd_{0.05}$, $Mo_{12}P_{1.5}V_{0.6}Cs_{1.0}Ni_{0.5}Cu_{0.25}Pd_{0.05}$, $Mo_{12}P_{1.5}V_{0.6}Cs_{1.5}Cu_{0.15}Zn_{0.1}Si_{0.05}$, $Mo_{12}P_{1.5}V_{0.6}Cs_{1.5}Cu_{0.25}Mn_{0.1}$, $Mo_{12}V_{1.0}P_{1.5}Cs_{1.0}Cu_{0.3}$, $Mo_{12}V_{1.0}P_{1.5}Cs_{1.0}Cu_{0.2}$, $Mo_{12}V_{1.0}P_{1.5}Cs_{1.0}Fe_{0.3}$, and mixtures of two or more of them in any ratios.

2. Nanocarbon Fiber Additive or Nanocarbon Fiber Modifier

The catalyst of the present disclosure comprises a nanocarbon fiber additive or nano-carbon fiber modifier dispersed in the primary catalyst. Based on the weight of the primary catalyst, the nanocarbon fiber modifier is added in an amount of 3-10%, preferably 4-9.5%, more preferably 5-9%, desirably 6-8%, advantageously 6.5-7.5%.

The inventors have found that if the nanocarbon fiber is added as an additive in a proportion of 3-10% by weight into the heteropolyacid primary catalyst, the catalytic activity of the catalyst can be improved significantly.

The nanocarbon fiber suitable for the present disclosure is not particularly limited, and may be selected from various commercially available nanocarbon fibers. In an embodiment of the present disclosure, the nanocarbon fiber is selected from the group consisting of a platelet-type nanocarbon fiber, a fishbone-type nanocarbon fiber, and a tube-type nanocarbon fiber; and the nanocarbon fiber is preferably a tube-type nanocarbon fiber.

In an embodiment of the present disclosure, the nanocarbon fiber is prepared by the following method: a nickel-iron alloy (nickel to iron weight ratio 2:1) supported on γ-$Al_2O_3$ with a loading mass fraction of 20% is used as a catalyst, and CO is used as a carbon source to synthesize a fishbone-type nanocarbon fiber. The synthesis is carried out in a horizontal quartz tube reactor. 1.0 g of the catalyst is reduced at 600° C. overnight with a hydrogen-argon mixed gas having a volume fraction of 25%. Then, a CO/$H_2$ mixed gas having a volume fraction of 80% is introduced (flow rate: 100 ml/min) for synthesis of 24 hours, and the yield of the nanocarbon fiber is about 20 g/g catalyst. The nanocarbon fiber is ultrasonically dispersed in 0.1 mol/l hydrochloric acid and soaked for two days, filtered and washed to neutrality, and then dried at 120° C. overnight.

In another example of the present disclosure, the nanocarbon fiber is prepared by catalytic chemical vapor deposition.

The nanocarbon fiber of the present disclosure has a diameter generally between 50-200 nm, preferably between 60-180 nm, more preferably 70-160 nm, desirably 80-140 nm, advantageously 90-120 nm, for example about 100 nm. When used, it can be added directly in a solid form to a reaction solution used for preparing the primary catalyst.

3. Support/Heat-Conducting Diluent

The catalyst of the present disclosure also comprises an oxide that doubles as a support and a heat-conducting diluent. In an embodiment of the present disclosure, the support/heat-conducting diluent is selected from one of SiC, $SiO_2$, $MoO_3$, $WO_3$, $TiO_2$ and mixtures thereof formed in any ratios; and the support/heat-conducting diluent is preferably one of or a mixture of more than one of SiC, $MoO_3$, and $TiO_2$.

Based on the weight of the primary catalyst, the support/heat-conducting diluent is used in an amount of 11.1-50%, preferably 15-45%, more preferably 20-40%, desirably 25-35%, advantageously 28-32%.

B. Method for Preparing the Catalyst

The method for manufacturing the catalyst of the present disclosure comprises the following steps:

i) Dissolving or suspending precursor compounds of the corresponding component elements in a solvent, mixing to obtain a solution or slurry, followed by addition of the nanocarbon fiber into the solution or slurry.

The precursor compounds of the catalyst elements used in the mixed solution or slurry are not particularly limited, and nitrates, carbonates, acetates, oxides, halides, oxides, oxyacid salts and the like of the constituent elements of the catalyst may be used.

Non-limiting examples of suitable molybdenum precursor compounds are, for example, molybdenum trioxide, ammonium paramolybdate, phosphomolybdic acid or molybdates, etc., preferably ammonium paramolybdate.

Non-limiting examples of suitable phosphorus precursor compounds are, for example, phosphorus pentoxide, phosphoric acid, phosphomolybdic acid, ammonium phosphate, etc., preferably phosphoric acid.

Non-limiting examples of suitable vanadium precursor compounds are, for example, vanadium pentoxide, ammonium metavanadate, etc., preferably ammonium metavanadate.

Non-limiting examples of suitable cesium precursor compounds are, for example, cesium nitrate, cesium chloride, cesium hydroxide, etc., preferably cesium nitrate.

There is no special requirement for the solvent or temperature for dissolving the precursor compounds, as long as the compounds used can be completely dissolved or uniformly mixed. In an embodiment of the present disclosure, the precursor compounds are dissolved or dispersed at a temperature in the range of 40-60° C.

Non-limiting examples of suitable solvents are, for example, water, ethanol, etc., and water is preferably used.

The proportions of the active components in the catalyst of the present disclosure are based on the atomic proportion of molybdenum, namely the atomic proportion of molybdenum being taken as 12. The proportion of phosphorus is 0.1-3, preferably 0.5-2.5, more preferably 1.0-2.3; the proportion of cesium is 0.01-3, preferably 0.1-2, more preferably 0.5-1.5; the proportion of vanadium is 0.01-5, preferably 0.02-4.5, more preferably 0.1-4; and the proportion of element D is 0.01-2, preferably 0.05-1.8, more preferably 0.1-1.3.

In an embodiment of the present disclosure, Solution A and Solution B are prepared first:

Solution A is formulated by dissolving at least compounds of molybdenum, phosphorus, and vanadium in a solvent. In addition to molybdenum, phosphorus and vanadium atoms, Solution A may also contain O atoms and ammonium radicals. Examples of suitable solvents include water, ethanol and the like, and water is preferably used. The amount of water is about 100-400 parts by weight, preferably 200-300 parts by weight, with the total amount of the compounds used to prepare the slurry being 100 parts by weight.

Solution B is prepared by dissolving a cesium compound and an element D-containing compound in a solvent. Examples of suitable solvents include water, ethanol and the like, and water is preferably used. The amount of water is about 200-800 parts by weight, preferably 300-400 parts by weight, with the total amount of the compounds used to prepare the slurry being 100 parts by weight.

Then, Solution A and Solution B are mixed, and a nanocarbon fiber is added.

(ii) Drying

The drying conditions and methods suitable for the method of the present disclosure are not particularly limited, and any drying method and drying temperature known in the art may be used. In an embodiment of the present disclosure, spray drying, evaporative drying, drum drying, etc. may be selected, with spray drying being preferred.

The dried catalyst blank may be crushed if so desired.

(ii) Mixing the Dried Blank with a Support/Heat-Conducting Diluent, Followed by Shaping and Baking Non-limiting examples of suitable heat-conducting diluents are, for example, one of or a mixture of more than one of SiC, $SiO_2$, $MoO_3$, $WO_3$, or $TiO_2$, preferably one of or a mixture of more than one of SiC, $MoO_3$, or $TiO_2$.

In a preferred embodiment of the present disclosure, based on the total weight of the primary catalyst, the support/heat-conducting diluent accounts for 11.1-50%, preferably 15-48%.

There is no special requirement for a mixing device suitable for mixing the heat-conducting diluent, and it may be any mixing device known in the art. In a preferred embodiment of the present disclosure, the mixing device is selected from the group consisting of a double-cone mixer, a multi-directional movement mixer, a trough type mixer, and the like.

In an embodiment of the present disclosure, the method of the present disclosure further comprises shaping the mixture of the catalyst blank mixture and the support/heat-conducting absorbent. There is no special requirement for the shaping method, and any shaping method known in the art may be used. In an embodiment of the present disclosure, the mixture is shaped by dry shaping or wet shaping. For example, tablet shaping, extrusion shaping, granulation shaping, etc. may be used. There is no special requirement for the shape of the shaped product. A shape such as cylindrical shape, ring shape, spherical shape or the like may be chosen as desired. In addition, a small amount of a lubricant, such as graphite or the like, may be added in the shaping process.

The catalyst blank is baked in an oxygen-containing atmosphere. The baking temperature is 300-450° C., preferably 350-400° C. The baking time is 60-600 minutes, preferably 120-540 minutes, more preferably 240-480 minutes.

In the oxygen-containing atmosphere suitable for the baking step of the present disclosure, the oxygen concentration is not less than 10% by mass, preferably not less than 20% by mass.

In an embodiment of the present disclosure, the catalyst is prepared as follows. Ammonium paramolybdate, ammonium metavanadate, and phosphoric acid are dissolved in warm water to obtain Solution A. Cesium nitrate and copper nitrate are dissolved in warm water to obtain Solution B. Solutions A and B are mixed at this temperature. After stirring to homogeneity, a nanocarbon fiber is added. After stirring, spray drying is conducted to obtain a dry material of the catalyst precursors which is crushed and then mixed with a support/heat-conducting diluent. After mixing uniformly, an appropriate amount of water is added, and extrusion shaping is conducted using a piston ram extruder to obtain an annular cylinder. The annular cylinder is then baked in an air stream to obtain a finished catalyst.

The catalyst of the present disclosure is suitable for synthesis of (meth)acrylic acid by gas-phase oxidation of (meth)acrolein. In an embodiment of the present disclosure, the synthesis method comprises:

preheating a mixture of a (meth)acrolein raw material, air (a diluent gas containing molecular oxygen) and water vapor; and passing the preheated mixture into a tubular fixed-bed reactor loaded with the catalyst of the present disclosure for selective oxidation reaction to synthesize (meth)acrylic acid.

In a suitable diluent gas containing molecular oxygen, the molecular oxygen may come from pure oxygen, oxygen-enriched air or air, and the diluent gas may be one of $N_2$, CO, $CO_2$ or $H_2O$ or a mixture therefore in any ratio.

In an embodiment of the present disclosure, the conditions for the oxidation reaction include:

a temperature in the range of 220-300° C., preferably 240-280° C.;

a pressure in the range of 0.05-0.5 MPa, preferably ambient pressure;

a total space velocity of the mixed gas of the raw materials for the reaction in the range of 1000-5000 $h^{-1}$, preferably 1200-3000 $h^{-1}$;

a molar concentration of (meth)acrylic acid in the range of 1-20%, preferably 3-8%;

a molar ratio of $O_2$ to (meth)acrolein in the range of 0.5-8, preferably 1-5; and a molar ratio of water vapor to (meth)acrolein in the range of 1-15, preferably 3-10.

C. Calculation Method of Catalytic Oxidation Reaction Results

The conversion and selectivity in the synthesis of (meth)acrylic acid by oxidation of (meth)acrolein are calculated as follows:

(Meth)acrolein conversion (mol %)=100×(moles of (meth)acrolein supplied−moles of (meth)acrolein leftover after the reaction)/moles of (meth)acrolein supplied (Meth)acrylic acid selectivity (mol %)=100×(moles of (meth)acrylic acid produced by the reaction)/(moles of (meth)acrolein supplied−moles of (meth)acrolein leftover after the reaction)

(Meth)acrylic acid yield (mol %)=100×(moles of (meth)acrylic acid produced by the reaction)/moles of (meth)acrolein supplied The method for preparing the high-performance catalyst and its catalytic performance for the selective oxidation of (meth)acrolein to produce (meth)acrylic acid will be illustrated with reference to the following specific examples, but the scope of the present disclosure is not limited to these examples.

Example 1

1200 g ammonium paramolybdate, 66.3 g ammonium metavanadate, and 97 g phosphoric acid were dissolved in 2400 g of distilled water at 60° C. to obtain Solution A. 110.4 g cesium nitrate and 32.2 g copper nitrate were dissolved in 400 g distilled water at 60° C. to obtain Solution B. Solutions A and B were mixed at this temperature. After stirring to homogeneity, 68 g tubular nanocarbon fiber (purchased from Dongguan Jinnai New Materials Co., Ltd.) was added. After stirring for 2 hours, spray drying was conducted to obtain a dry material of the catalyst precursors which was crushed and mixed with 525 g $TiO_2$ as a support/heat-conducting diluent. After mixing uniformly, an appropriate amount of water was added, and extrusion shaping was conducted using a piston ram extruder to obtain an annular cylinder having an outer diameter of 5 mm, a through-hole inner diameter of 1.5 mm, and a length of 5 mm. Then, baking was conducted in an air stream at 380° C. for 6 hours to obtain a finished catalyst. The elemental composition of the obtained catalyst except for oxygen is shown below.

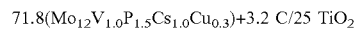

71.8($Mo_{12}V_{1.0}P_{1.5}Cs_{1.0}Cu_{0.3}$)+3.2 C/25 $TiO_2$ 1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 92.1%, and the MAA selectivity was 91.4%. When the reaction continued for 2000 hours under these conditions, the analysis results showed that the MAL conversion was 91.9% and the MAA selectivity was 91.5%. The catalyst exhibited no degradation.

Example 2

The 32.2 g copper nitrate in Example 1 was replaced with 21.5 g copper nitrate, and the other preparation conditions were unchanged. The elemental composition of the obtained catalyst except for oxygen is shown below.

71.8($Mo_{12}V_{1.0}P_{1.5}Cs_{1.0}Cu_{0.2}$)+3.2 C/25 $TiO_2$ 1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 87.5%, and the MAA selectivity was 92.3%. When the reaction continued for 2000 hours under these conditions, the analysis results showed that the MAL conversion was 87.1% and the MAA selectivity was 92.4%. The catalyst exhibited no degradation.

Example 3

1300 g particles of the catalyst obtained in Example 2 were loaded directly into a tubular fixed-bed reactor having a diameter of 25 mm and a length of 3 m. The selective oxidation reaction was conducted at 270° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 94.5%, and the MAA selectivity was 89.3%. When the reaction was continued for 2000 hours under these conditions, the analysis results showed that the MAL conversion was 94.0% and the MAA selectivity was 89.2%. The catalyst exhibited no degradation.

Example 4

The 32.2 g copper nitrate in Example 1 was replaced with 41.5 g ferric nitrate, and the other preparation conditions were unchanged. The elemental composition of the obtained catalyst except for oxygen is shown below.

71.8($Mo_{12}V_{1.0}P_{1.5}Cs_{1.0}Fe_{0.3}$)+3.2 C/25 $TiO_2$ 1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 After 80 hours of reaction, the reaction product was sampled and analyzed using gas chromatography. The MAL conversion was 95.2%, and the MAA selectivity was 88.5%.

When the reaction continued for 2000 hours under these conditions, the analysis results showed that the MAL conversion was 94.7% and the MAA selectivity was 88.7%. The catalyst exhibited no degradation.

Example 5

The 68 g tubular nanocarbon fiber in Example 1 was replaced with 132 g platelet nanocarbon fiber, and the other preparation conditions were unchanged. The elemental composition of the obtained catalyst except for oxygen is shown below.

$$69.6(Mo_{12}V_{1.0}P_{1.5}Cs_{1.0}Cu_{0.3})+6.1\ C/24.3\ TiO_2$$

1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 93.1%, and the MAA selectivity was 89.0%. When the reaction continued for 2000 hours under these conditions, the analysis results showed that the MAL conversion was 89.0% and the MAA selectivity was 89.0%. The catalyst exhibited no degradation.

Comparative Example 1

The nanocarbon fiber in Example 1 was dispensed with, and the other preparation conditions were unchanged. The elemental composition of the obtained catalyst except for oxygen is shown below.

$$75(Mo_{12}V_{1.0}P_{1.5}Cs_{1.0}Cu_{0.3})/25\ TiO_2$$

1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 85.1%, and the MAA selectivity was 89.0%. When the reaction continued for 2000 hours under these conditions, the analysis results showed that the MAL conversion was 84.6% and the MAA selectivity was 88.7%.

Comparative Example 2

The 68 g tubular nanocarbon fiber in Example 1 was replaced with 68 g graphite having a micro-sized particle diameter, and the other preparation conditions were unchanged. The elemental composition of the obtained catalyst except for oxygen is shown below.

$$71.8(Mo_{12}V_{1.0}P_{1.5}Cs_{1.0}Cu_{0.3})+3.2\ C/25\ TiO_2$$

1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 86.1%, and the MAA selectivity was 88.7%. When the reaction continued for 2000 hours under these conditions, the analysis results showed that the MAL conversion was 85.4% and the MAA selectivity was 89.0%.

Comparative Example 3

The 525 g TiO$_2$ in Example 1 was replaced with 525 g ZrO$_2$, and the other preparation conditions were unchanged. The elemental composition of the obtained catalyst except for oxygen is shown below.

$$71.8(Mo_{12}V_{1.0}P_{1.5}Cs_{1.0}Cu_{0.3})+3.2\ C/25\ ZrO_2$$

1300 g particles of the catalyst were loaded directly into a tubular fixed-bed reactor having a diameter of 25 mm and a length of 3 m. The selective oxidation reaction was conducted at 260° C. (reaction temperature), ambient pressure, MAL:$O_2$:$N_2$:$H_2O$=1:2:8:10, and a space velocity of 1500 $h^{-1}$. After 80 hours of reaction, the reaction product was sampled and analyzed using gas chromatography. The MAL conversion was 92.1%, and the MAA selectivity was 87.2%. When the reaction continued for 2000 hours under these conditions, the analysis results showed that the MAL conversion was 92.0% and the MAA selectivity was 86.9%.

Example 6

1300 g particles of the catalyst obtained in Example 1 were loaded directly into a tubular fixed-bed reactor having a diameter of 25 mm and a length of 3 m. The selective oxidation reaction was conducted at 260° C. (reaction temperature), ambient pressure, MAL:$O_2$: $N_2$: $H_2O$=1:2:8:10, and a space velocity of 1200 $h^{-1}$. After 80 hours of reaction, the reaction product was sampled and analyzed using gas chromatography. The MAL conversion was 94.6%, and the MAA selectivity was 90.8%. When the reaction was continued for 2000 hours under these conditions, the analysis results showed that the MAL conversion was 94.2% and the MAA selectivity was 90.3%. The catalyst exhibited no degradation.

Comparative Example 4

The 68 g tubular nanocarbon fiber in Example 1 was replaced with 350 g tubular nanocarbon fiber, and the other preparation conditions were unchanged. The elemental composition of the obtained catalyst except for oxygen is shown below.

$$63.3(Mo_{12}V_{1.0}P_{1.5}Cs_{1.0}Cu_{0.3})+14.7\ C/22\ TiO_2$$

The catalyst was found to be relatively loose and difficult to shape. It was eventually given up for the catalytic oxidation reaction.

What is claimed is:

1. A heteropolyacid catalyst for preparing (meth)acrylic acid by oxidation of (meth)acrolein, wherein the catalyst has a composition represented by the following formula:

$$x(Mo_{12}P_aCs_bV_cD_eO_f)+tC/yZ$$

wherein $Mo_{12}P_aCs_bV_cD_eO_f$ is a primary catalyst of heteropolyacid salt, C is a nanocarbon fiber additive, and Z is a support/heat conducting diluent;

Mo, P, Cs, V and O represent elements of molybdenum, phosphorus, cesium, vanadium and oxygen respectively;

D represents at least one element selected from the group consisting of copper, iron, magnesium, manganese, antimony, zinc, tungsten, silicon, nickel, and palladium;

Z is selected from the group consisting of SiC, SiO$_2$, MoO$_3$, WO$_3$, TiO$_2$, and mixtures thereof in any ratios;

a, b, c, e, and f represent the atomic proportions of the elements, wherein a=0.1-3, b=0.01-3, c=0.01-5, e=0.01-2, and f is an atomic proportion of oxygen needed to satisfy the valences of the above components;

x, y represent the weights of the primary catalyst and the support/heat-conducting diluent Z, wherein y/x=11.1-50%;

t represents a weight of the nanocarbon fiber, t/x=3-10%; and wherein the nanocarbon fiber has a diameter between 50-200 nm.

2. The heteropolyacid catalyst of claim 1, wherein:
a=0.3-2.5;
b=0.05-2.5;
c=0.05-4; and
e=0.05-1.8.

3. The heteropolyacid catalyst of claim 1, wherein the primary catalyst is selected from the group consisting of $Mo_{12}P_{1.5}V_{0.6}Cs_{1.5}Cu_{0.3}$, $Mo_{12}P_{1.5}V_{0.6}Cs_{1.5}Zn_{0.3}Pd_{0.05}$, $Mo_{12}P_{1.5}V_{0.6}Cs_{1.5}Cu_{0.3}Sb_{0.2}$, $Mo_{12}P_{1.5}V_{0.6}Cs_{1.5}Zn_{0.3}W_{0.2}$, $Mo_{12}P_{1.5}V_{0.6}Cs_{1.5}Cu_{0.3}Mg_{0.2}$, $Mo_{12}P_{1.5}V_{0.6}Cs_{1.5}Cu_{0.25}Pd_{0.05}$, $Mo_{12}P_{1.5}V_{0.6}Cs_{1.0}Ni_{0.5}Cu_{0.25}Pd_{0.05}$, $Mo_{12}P_{1.5}V_{0.6}Cs_{1.5}Cu_{0.15}Zn_{0.1}Si_{0.05}$, $Mo_{12}P_{1.5}V_{0.6}Cs_{1.5}Cu_{0.25}Mn_{0.1}$, $Mo_{12}V_{1.0}P_{1.5}Cs_{1.0}Cu_{0.3}$, $Mo_{12}V_{1.0}P_{1.5}Cs_{1.0}Cu_{0.2}$, $Mo_{12}V_{1.0}P_{1.5}Cs_{1.0}Fe_{0.3}$, and mixtures of two or more of them.

4. The heteropolyacid catalyst of claim 1, wherein the nanocarbon fiber additive is added in an amount of 4-9.5% based on the weight of the primary catalyst.

5. The heteropolyacid catalyst of claim 1, wherein the nanocarbon fiber is selected from the group consisting of a platelet-type nanocarbon fiber, a fishbone-type nanocarbon fiber, and a tube-type nanocarbon fiber.

6. The heteropolyacid catalyst of claim 1, wherein the nanocarbon fiber is a tube-type nanocarbon fiber.

7. A method for preparing the heteropolyacid catalyst of claim 1, comprising:
(a) stoichiometrically mixing a molybdenum precursor compound solution, a phosphorus precursor compound solution and a vanadium precursor compound solution to form Solution A; and stoichiometrically mixing a cesium precursor compound solution and a copper precursor compound solution to form Solution B;
(b) mixing Solution A and Solution B, adding nanocarbon fiber, and drying to form a dried body; and
(c) mixing the dried body with a support/heat-conducting diluent, following by shaping and baking.

8. The method of claim 7, wherein the method comprises:
dissolving ammonium paramolybdate, ammonium metavanadate and phosphoric acid it warm water to obtain Solution A;
dissolving cesium nitrate and copper nitrate in warm water to obtain Solution B;
mixing Solutions A and B at this temperature, adding a nanocarbon fiber after stirring to homogeneity, and spray drying after stirring to obtain a dry material of the catalyst precursors which is crushed and then mixed with a support/heat-conducting diluent, followed by addition of an appropriate amount of water after mixing uniformly, followed by extrusion shaping using a piston ram extruder to obtain an annular cylinder; and
baking the annular cylinder in an air stream to obtain a finished catalyst.

9. The method of claim 7, wherein the nanocarbon fiber is selected from the group consisting of a platelet-type nanocarbon fiber, a fishbone-type nanocarbon fiber, and a tube-type nanocarbon fiber.

10. A method of using the catalyst of claim 1, comprising preparing (meth)acrylic acid by performing an oxidation reaction of (meth)acrolein using the catalyst.

* * * * *